United States Patent [19]

Fuso

[11] Patent Number: 5,786,476

[45] Date of Patent: Jul. 28, 1998

[54] UV ABSORBERS, THEIR PREPARATION AND USE

[75] Inventor: Francesco Fuso, Therwil, Switzerland

[73] Assignee: Ciba Specialty Chemicals Corporation, Tarrytown, N.Y.

[21] Appl. No.: 814,303

[22] Filed: Mar. 10, 1997

[30] Foreign Application Priority Data

Mar. 12, 1996 [CH] Switzerland ............... 641/96

[51] Int. Cl.$^6$ ........................... C07D 251/54
[52] U.S. Cl. ........................... 544/208; 544/209
[58] Field of Search ........................... 544/208, 209

[56] References Cited

U.S. PATENT DOCUMENTS

| | | | |
|---|---|---|---|
| 3,041,330 | 6/1962 | Coleman et al. | 260/231 |
| 5,098,445 | 3/1992 | Hung et al. | 8/507 |
| 5,274,083 | 12/1993 | Herd et al. | 544/208 |
| 5,340,928 | 8/1994 | Hoppe et al. | 544/208 |

FOREIGN PATENT DOCUMENTS

| | | | |
|---|---|---|---|
| 3103110 | 8/1982 | Germany | 544/208 |
| 3917046 | 11/1990 | Germany | 544/208 |
| 0199878 | 12/1982 | Japan | 544/208 |
| 9404515 | 3/1994 | WIPO . | |

*Primary Examiner*—Yogendra N. Gupta
*Attorney, Agent, or Firm*—David R. Crichton

[57] ABSTRACT

The invention relates to compounds of formula

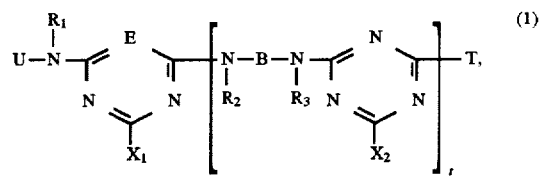

wherein the variables are as claimed in the claims. The compounds are suitable as UV absorbers for the photochemical stabilisation of undyed or dyed cellulosic fibre materials for enhancing their sun protection factor.

15 Claims, No Drawings

UV ABSORBERS, THEIR PREPARATION AND USE

The present invention relates to novel fibre-reactive UV absorbers, to a process for their preparation and to the use thereof for the photochemical stabilisation of undyed and dyed textile fibres and for enhancing the sun protection factor of such textile fibres.

That UV radiation is harmful to the skin is known. Protection against strong solar radiation is usually afforded by applying a composition that contains a UV absorber (sun cream) direct to the skin. In particularly sunny parts of the world, as in Australia and America, there has recently been a drastic increase in the incidence of skin damage induced by UV radiation. In these countries, increased attention is hence being paid to the problem of protecting the skin from solar radiation.

The proposal has been made not just to protect the skin direct, but also to provide clothing surrounding the skin as well as textile sun protective articles such as marquees or sunshades with additional protection against UV radiation. Most natural and synthetic textile fabrics, whether undyed or dyed, are usually at least partially permeable to UV radiation, so that the mere wearing of clothing does not afford adequate protection of the skin from damage induced by UV radiation. Remedy is possible here by incorporating UV absorbers in textile fabric.

The results obtained in the field of textile materials, especially materials containing cellulosic fibres or natural or synthetic polyamide fibres, which respect to protection from UV radiation, have so far not been satisfactory, and there is a need to develop novel UV absorbers specially tailored to these materials.

Accordingly, the invention relates to compounds of formula

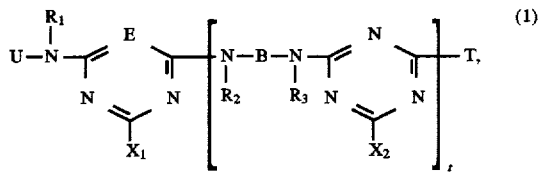

wherein

B is an aliphatic, cycloaliphatic, aromatic or aromaticaliphatic linking group or, together with —NR$_2$— and —NR3—, forms a heterocyclic ring, R$_1$, R$_2$ and R$_3$ are each independently of the other hydrogen or unsubstituted or substituted C$_1$–C$_4$alkyl, =E— is a =N— or =C(T$_1$)— group, and T$_1$ is halogen, C$_1$–C$_4$alkylsulfonyl, formyl, C$_2$–C$_4$alkoxycarbonyl or cyano, U is the radical of a UV absorber of formula

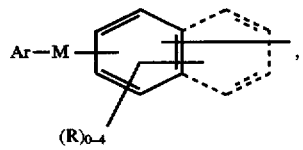

M is a —CO—NR'—, —NR'—CO—NR'— or —SO$_2$—NR'— group, R' s hydrogen or C$_1$–C$_4$alkyl, (R)$_{0-4}$ denotes 0 to 4 identical or different radicals R selected from the group consisting of sulfo, C$_1$–C$_4$alkyl, C$_1$–C$_4$alkoxy, carboxy, hydroxy and halogen, Ar is a phenyl, naphthyl or styryl radical which may be further substituted, X$_1$ and X$_2$ are each independently of the other halogen, hydroxy, unsubstituted or substituted amino, 3-carboxypyridin-1-yl or 3-carbamoylpyridin-1-yl, T independently has one of the meanings given for X$_1$ or is a radical U'—NR$_1$'—, wherein U' and R$_1$' each independently of the other have the meaning given above for U and R$_1$, or is an alkoxy, aryloxy, alkylthio or arylthio radical which may be further substituted, or a nitrogen-containing heterocyclic radical, or a reactive radical of formula

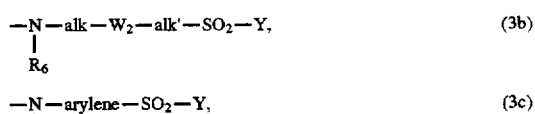

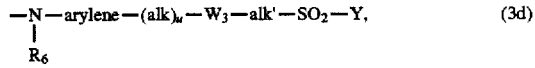

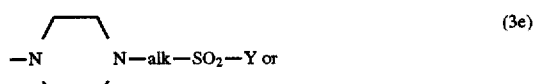

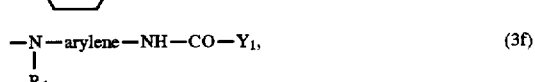

R$_4$ is hydrogen, C$_1$–C$_4$alkyl which is unsubstituted or substituted by hydroxy, sulfo, sulfato, carboxy or cyano, or a radical

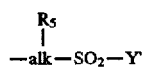

R$_5$ is hydrogen, hydroxy, sulfo, sulfato, carboxy, cyano, halogen, C$_1$—C$_4$alkoxycarbonyl, C$_1$–C$_4$alkanoyloxy, carbamoyl or the —SO$_2$—Y group, R$_6$ is hydrogen or C$_1$–C$_4$alkyl, alk and alk' are each independently of the other C$_1$–C$_6$alkylene, arylene is a phenylene or naphthylene radical which is unsubstituted or substituted by sulfo, carboxy, C$_1$–C$_4$alkyl, C$_1$–C$_4$alkoxy or halogen, Y is vinyl or a radical —CH$_2$—CH$_2$—G, and G is a leaving group, Y$_1$ is the radical —CHBr—CH$_2$—Br or —CBr=CH$_2$, W$_2$ is the radical —O— or —NR$_6$—, W$_3$ is a —SO$_2$—NR$_4$—, —CONR$_4$— or —NR$_4$CO— group, wherein R$_4$ has the meaning given above, and t and u are each independently of the other 0 or 1, with the proviso that the compounds of formula (1) carry at least one sulfo or sulfato group and at least one group which is removable with alkali.

Variable =E— is preferably the =N—group.

B defined as an aliphatic linking group may be straight-chain or branched C$_2$–C$_{12}$alkylene which is unsubstituted or substituted by hydroxy, sulfo or sulfato and/or interrupted by —O—. B is preferably straight-chain or branched C$_2$–C$_6$alkylene which is unsubstituted or substituted by hydroxy, sulfo or sulfato. Illustrative examples of particularly preferred alkylene radicals B are 1,2-ethylene, 1,2-propylene, 1,3-propylene, 2-hydroxy-1,3-propylene, 2,2-dimethyl-1,3-propylene, 1,4-butylene, 2-methyl-1,5-pentylene and 1,6-hexylene.

B defined as cycloaliphatic linking group is suitably e.g. cyclohexylene or the radical of formula

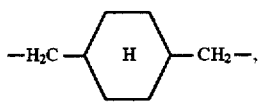

(4)

or —NR— and —NR'—, together with B, form a ring, typically a piperazine ring.

Illustrative examples of aromatic linking groups B are 1,2-, 1,3- or 1,4-phenylene, each of which is unsubstituted or substituted by e.g. sulfo, carboxy, $C_1$–$C_4$alkyl, $C_1$–$C_4$alkoxy or halogen, unsubstituted or sulfo-substituted naphthylene, or a radical of formula

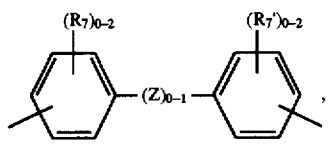

(5)

wherein Z may have the meaning of —CO—, —NHCO—, —NHCONH—, —(CH$_2$)$_{1-4}$—, —NH—, —CH=CH—, —O—, —SO$_2$— or —N=N—, and (R$_7$)$_{0-2}$ and (R$_7$')$_{0-2}$ are each independently of the other 0 to 2 identical or different radicals selected from the group consisting of sulfo, methyl, methoxy and chloro.

The aromatic linking group B is preferably 1,3- or 1,4-phenylene which is unsubstituted or substituted by sulfo, carboxy, chloro, methyl or methoxy, naphthylene which is substituted by 1 or 2 sulfo groups, or a radical of formula

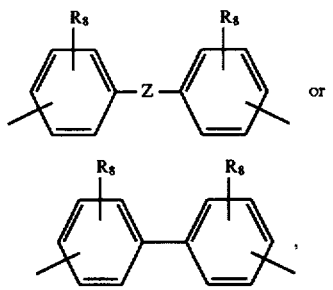

(5a)

(5b)

wherein Z is —NHCONH—, —O—, —NH—, —CH=CH— or —CH$_2$—, and R$_8$ is hydrogen or sulfo.

Illustrative examples of particularly preferred aromatic linking groups B are 1,3-phenylene, 1,4-phenylene, 4-methyl-1,3-phenylene, 4-sulfo-1,3-phenylene, 3-sulfo-1,4-phenylene, 3,6-disulfo-1,4-phenylene, 4,6-disulfo-1,3-phenylene, 3,7-disulfo-1,5-naphthylene, 4,8-disulfo-2,6-naphthylene, 2,2'-disulfo-4,4'-diphenylene, 4,4'phenyleneurea-2,2'-disulfonic acid or 2,2'-disulfo-4,4'-stilbenylene and, in particular, 1,3-phenylene, 1,4-phenylene, 4-sulfo-1,3-phenylene, 3-sulfo-1,4-phenylene, 3,6-disulfo-1,4-phenylene or 4,6-disulfo-1,3-phenylene.

Typical examples of aromatic-aliphatic linking groups B are phenylene-$C_1$–$C_4$alkylene which is unsubstituted or substituted in the phenylene moiety by e.g. sulfo, methyl, methoxy, carboxy or chloro. B defined as aromatic-aliphatic linking group is preferably phenylenemethylene which is unsubstituted or substituted in the phenylene moiety by sulfo, methyl or methoxy.

B is preferably $C_2$–$C_6$alkylene which is unsubstituted or substituted by hydroxy, sulfo or sulfato, 1,3- or 1,4-phenylene which is unsubstituted or substituted by sulfo, carboxy, chloro, methyl or methoxy, naphthylene which is substituted by 1 or 2 sulfo groups, or a radical of formula

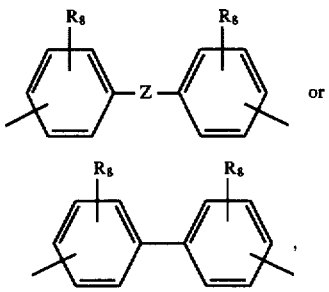

(5a)

(5b)

wherein Z is —NHCONH—, —O—, —NH—, —CH=CH— or —CH$_2$—, and R$_8$ is hydrogen or sulfo.

B is particularly preferably 1,3-phenylene, 1,4-phenylene, 4-sulfo-1,3-phenylene, 3-sulfo-1,4-phenylene, 3,6-disulfo-1,4-phenylene or 4,6-disulfo-1,3-phenylene.

R$_1$, R$_2$ and R$_3$ are each independently of one another typically hydrogen or $C_1$–$C_4$alkyl which is unsubstituted or substituted by e.g. halogen, hydroxy, cyano, $C_1$–$C_4$alkoxy, $C_1$–$C_4$alkoxycarbonyl, carboxy, sulfamoyl, sulfo or sulfato. R$_1$, R$_2$ and R$_3$ are preferably each independently of one another hydrogen or $C_1$–$C_4$alkyl and, particularly preferably, hydrogen, methyl or ethyl.

X$_1$ or X$_2$ in formula (1) defined as unsubstituted or substituted amino is typically —NH$_2$, N-mono- or N,N-di-$C_1$–$C_4$alkylamino which is unsubstituted or substituted in the alkyl moiety by e.g. hydroxy, carboxy, sulfo, sulfato or $C_1$–$C_4$alkoxy, cyclohexylamino, or phenylamino or N—$C_1$—$C_4$alkyl-N-phenylamino which is unsubstituted or substituted in the phenyl moiety by e.g. $C_1$–$C_4$alkyl, $C_1$–$C_4$alkoxy, carboxy, sulfo, halogen or by a radical of formula —SO$_2$—Y (6a), —CONH—(CH$_2$)$_p$—SO$_2$—Y (6b), wherein Y has the meaning stated above, and p is an integer from 1 to 6.

p in formula (6b) is preferably 2, 3 or 4 and, particularly preferably, 2 or 3.

X$_1$ and X$_2$ defined as unsubstituted or substituted amino are each independently of the other preferably amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, or phenylamino which is substituted by a radical of formula (8a) or (8b). X$_1$ and X$_2$ defined as unsubstituted or substituted amino are each independently of the other particularly preferably amino, β-sulfoethylamino, β-hydroxyethylamino, N,N-di-β-hydroxyethylamino and o-, m- or p-sulfophenylamino.

X$_1$ and X$_2$ are each independently of the other preferably chloro, fluoro, hydroxy or amino, N-mono- or N,N-di-$C_1$–$C_4$alkylamino which is unsubstituted or substituted in the alkyl moiety by hydroxy, sulfo or sulfato, or phenylamino which is unsubstituted or substituted in the phenyl moiety by methyl, ethyl, methoxy, ethoxy, carboxy, sulfo, chloro or by a radical of formula (8a) or (8b).

X$_1$ and X$_2$ are each independently of the other particularly preferably chloro or fluoro and, most preferably, chloro.

The phenyl, naphthyl or styryl radical Ar in formula (2) can be further substituted by, for example, $C_1$–$C_4$alkyl; $C_1$–$C_4$alkoxy; phenoxy which is unsubstituted or substituted e.g. by $C_1$-$C_4$alkyl, $C_1$-$C_4$alkoxy, halogen or sulfo; sulfo; carboxy; hydroxy; halogen; nitro; cyano; trifluoromethyl; $C_1$-$C_4$alkoxycarbonyl, typically methoxycarbonyl or ethoxycarbonyl; formyl, $C_2$-$C_4$alkanoyl, typically acetyl, propionyl; benzoyl, $C_2$-$C_4$alkylcarbonyloxy, typically acetoxy; sulfamoyl; $C_2$-$C_4$alkanoylamino, typically acetylamino, propionylamino; benzoylamino; n-mono- or N,N-di-$C_1$-$C_4$alkylsulfamoyl; N-phenylsulfamoyl; $C_1$-$C_4$alkylthio; phenylthio; $C_1$-$C_4$alkylsulfonylamino; or phenylsulfonylamino.

Preferred substituents of the phenyl, naphthyl or styryl radical Ar are methyl, ethyl, methoxy, ethoxy, chloro, sulfo, nitro, hydroxy, carboxy, methoxycarbonyl or ethoxycarbonyl. Particularly preferred substituents of the phenyl, naphthyl or styryl radical Ar are methyl, methoxy, sulfo, hydroxy, carboxy or methoxycarbonyl.

Ar is preferably a phenyl radical which is unsubstituted or substituted by methyl, ethyl, methoxy, ethoxy, chloro, sulfo, nitro, hydroxy, carboxy, methoxycarbonyl or ethoxycarbonyl, or an unsubstituted or sulfo- or hydroxy-substituted naphthyl radical, or the styryl radical. Ar is particularly preferably a phenyl radical which is unsubstituted or substituted by methyl, methoxy, sulfo, hydroxy, carboxy or methoxycarbonyl.

The variable $(R)_{0-4}$ denotes preferably 0 to 4 identical or different radicals selected from the group consisting of sulfo, methyl, methoxy, carboxy and hydroxy.

R' is preferably hydrogen, methyl or ethyl and, most preferably, hydrogen.

M is preferably the —CONH—, —NH—CO—NH— or —SO$_2$NH— group and, most preferably, the —CONH— group.

U is preferably a radical of formula

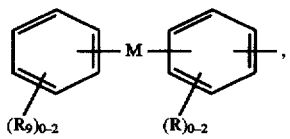

(2a)

wherein $(R_9)_{0-2}$ denotes 0 to 2 identical or different radicals $R_9$ selected from the group consisting of methyl, ethyl, methoxy, ethoxy, chloro, sulfo, nitro, hydroxy, carboxy, methoxycarbonyl or ethoxycarbonyl, and $(R)_{0-2}$ denotes 0 to 2 identical or different radicals R selected from the group consisting of sulfo, methyl, methoxy, carboxy and hydroxy, and M is a —CO—NR'—, —NR'—CO—NR'— or —SO$_2$—NR'— group, wherein R' has the meanings and preferred meanings given above. U is particularly preferably a radical of the above formula (2a), wherein $(R_9)_{0-2}$ denotes 0 to 2 identical or different radicals $R_9$ selected from the group consisting of methyl, methoxy, sulfo, hydroxy, carboxy or methoxycarbonyl, and $(R)_{0-2}$ denotes 0 to 2 identical or different radicals R selected from the group consisting of sulfo, methyl, methoxy, carboxy and hydroxy, and M is a —CONH— group.

If T independently has one of the meanings given above for $X_1$, then the preferred meanings given above apply independently.

If T is a radical U'—NR$_1$'—, then the meanings and preferred meanings given above for U and R$_1$ apply independently. The radicals U—NR$_1$— and U'—NR$_1$' are different or, preferably, identical.

T defined as an alkoxy radical is preferably a $C_1$-$C_4$alkoxy radical, typically methoxy, ethoxy, n- or isopropoxy or n-, iso-, sec- or tert-butoxy. The preferred meanings are methoxy and isopropoxy.

T defined as aryloxy radical is typically phenoxy which is unsubstituted or substituted by e.g. $C_1$-$C_4$alkyl, $C_1$-$C_4$alkoxy, halogen, hydroxy, carboxy or sulfo.

T defined as alkylthio radical is typically $C_1$-$C_4$alkylthio and, preferably, methylthio or ethylthio.

T defined as an arylthio radical is typically phenyltio which is unsubstituted or substituted by e.g. $C_1$-$C_4$alkyl, $C_1$-$C_4$alkoxy, halogen, hydroxy, carboxy or sulfo.

T defined as a nitrogen-containing heterocyclic radical is typically the piperidino or piperazino radical or, preferably, the morpholino radical.

Suitable leaving groups G in the radicals of formulae (3a)–(3e), (6a) and (6b) are typically —Cl, —Br, —F, —OSO$_3$H, —SSO$_3$H, —OCO—CH$_3$, —OPO$_3$H$_2$, —OCO—CCl$_3$, —OCO—CHCl$_2$, —OCO—CH$_2$Cl, —OSO$_2$—C$_1$-$C_4$-alkyl, —OSO$_2$—N(C$_1$-$C_4$-alkyl)$_2$ or —OCO—C$_6$H$_5$.

G is preferably a group of formula —Cl, —OSO$_3$H, —SSO$_3$H, —OCO—CH$_3$, —OCO—C$_6$H$_5$ or —OPO$_3$H$_2$, particularly preferably —Cl or —OSO$_3$H, most preferably —OSO$_3$H.

Y is preferably vinyl, β-chloroethyl, β-sulfatoethyl, β-thiosulfatoethyl, β-acetoxyethyl, β-phenoxyethyl or β-phosphatoethyl and, particularly preferably, β-sulfatoethyl or vinyl.

alk and alk' are each independently of the other typically a methylene, ethylene, 1,3-propylene, 1,4-butylene, 1,5-pentylene or 1,6-hexylene radical or the branched isomers thereof.

alk and alk' are each independently of the other preferably a $C_1$-$C_4$alkylene radical and, particularly preferably, an ethylene radical or a 1,2- or 1,3-propylene radical.

arylene is preferably a 1,3- or 1,4-phenylene radical which is unsubstituted or substituted by e.g. sulfo, methyl, methoxy or carboxy, or an unsubstituted or sulfo-substituted naphthylene radical and, particularly preferably, an unsubstituted 1,3- or 1,4-phenylene radical.

$R_4$ is preferably hydrogen or $C_1$-$C_4$alkyl such as methyl, ethyl, propyl, isopropyl, butyl, isobutyl, sec-butyl or tert-butyl. $R_4$ is particularly preferably hydrogen.

$R_5$ is preferably hydrogen.

$R_6$ is preferably hydrogen, methyl or ethyl, most preferably hydrogen.

$W_2$ is preferably —NH— or —O— and, most preferably, —O—.

$W_3$ is preferably a group of formula —CONH— or —NHCO—, most preferably a group of formula —CONH—.

u is preferably 0.

A reactive radical T is preferably a radical of formulae (3a) to (3f) above, wherein $W_3$ is a group of formula —CONH— or —NHCO—, $R_4$, $R_5$ and $R_6$ are each hydrogen, $W_2$ is the radical —O— or —NH—, alk and alk' are each independently of the other ethylene or propylene, arylene is phenylene which is unsubstituted or substituted by methyl, methoxy, carboxy or sulfo, or unsubstituted or sulfo-substituted naphthylene, Y is vinyl or β-sulfatoethyl, and u is 0.

Particularly preferred fibre-reactive radicals T are those of formula

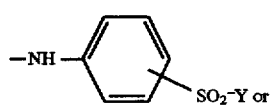

(3c')

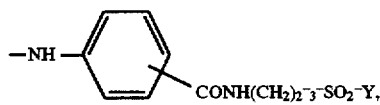

(3d')

wherein Y is vinyl or β-sulfatoethyl.

Preferred meanings of T are amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, mono-, di- or trisulfonaphthylamino, morpholino or a radical —NR$_1$—U, wherein R$_1$ and U each have the meaning given above, or a radical of formulae (3a) to (3f) above, wherein W$_3$ is a group of formula —CONH— or —NHCO—, R$_4$, R$_5$ and R$_6$ is each hydrogen, W$_2$ is the radical —O— or —NH—, alk and alk' are each independently of the other ethylene or propylene, arylene is phenylene which is unsubstituted or substituted by methyl, methoxy, carboxy or sulfo, or unsubstituted or sulfo-substituted naphthylene, Y is vinyl or β-sulfatoethyl, and u is 0.

T is particularly preferably a radical of formula —NR$_1$—U, wherein R$_1$ and U each have the meanings and preferred meanings given above, or a radical of formula (3c') above.

One group of preferred compounds is that of formula

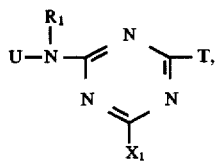
(1a)

wherein R$_1$, T, U and X$_1$ each have the meanings and preferred meanings given above.

Of these compounds of formula (1a), those are particularly preferred, wherein X$_1$ is chloro or fluoro, T is amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, mono-, di- or trisulfonaphthylamino, morpholino or a radical —NR$_1$—U, or a radical of formulae (3a) to (3e) above, wherein W$_3$ is a group of formula —CONH— or —NHCO—, R$_4$, R$_5$ and R$_6$ are each hydrogen, W$_2$ is the radical —O— or —NH—, alk and alk' are each independently of the other ethylene or propylene, arylene is phenylene which is unsubstituted or substituted by methyl, methoxy, carboxy or sulfo, or unsubstituted or sulfo-substituted naphthylene, Y is vinyl or β-sulfatoethyl, and u is 0, R is hydrogen, and U is a radical of formula

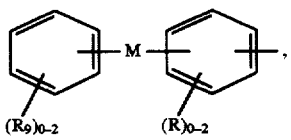
(2a)

wherein (R$_9$)$_{0-2}$ denotes 0 to 2 identical or different radicals R$_9$ selected from the group consisting of methyl, ethyl, methoxy, ethoxy, chloro, sulfo, nitro, hydroxy, carboxy, methoxycarbonyl or ethoxycarbonyl, and (R)$_{0-2}$ denotes 0 to 2 identical or different radicals R selected from the group consisting of sulfo, methyl, methoxy, carboxy and hydroxy, and M is a —CO—NR'—, —NR'—CO—NR'— or —SO$_2$—NR'— group, wherein R' is hydrogen, methyl or ethyl.

A particularly preferred embodiment of this invention relates to compounds of formula (1a) above, wherein R$_1$ is hydrogen, X$_1$ is chloro, T is a radical —NH—U or a radical of formula

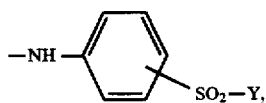
(3c')

wherein Y is vinyl or β-sulfatoethyl, and U is a radical of formula (2a) above, wherein (R$_9$)$_{0-2}$ denotes 0 to 2 identical or different radicals R$_9$ selected from the group consisting of methyl, methoxy, sulfo, hydroxy, carboxy and methoxycarbonyl, and (R)$_{0-2}$ denotes 0 to 2 identical or different radicals R selected from the group consisting of sulfo, methyl, methoxy, carboxy and hydroxy, and M is a —CONH— group.

Another group of preferred compounds is that of formula

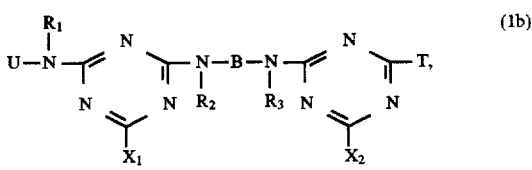
(1b)

wherein B, R$_1$, R$_2$, R$_3$, T, U, X$_1$ and X$_2$ each have the meanings and preferred meanings given above.

Of the compounds of formula (1b), those are particularly preferred, wherein T is unsubstituted or substituted amino, morpholino, C$_1$-C$_4$alkoxy or a radical U—NR$_1$—, wherein U and R$_1$ have the meanings and preferred meanings given above.

Of the compounds of formula (1b), those are particularly preferred, wherein T is a radical —U—NR$_1$, wherein U and R$_1$ each have the meanings and preferred meanings given above, or amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, or phenylamino which is substituted by a radical of formula (6a) or (6b) above.

Particularly preferred compounds of formula (1b) are those, wherein T is a radical —U—NH—, wherein U has the meanings and preferred meanings given above.

A preferred embodiment of this invention relates to compounds of formula

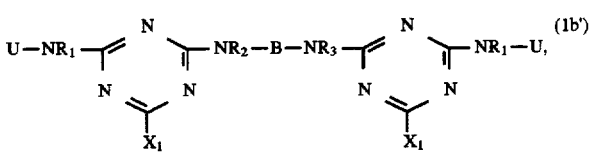
(1b')

wherein R$_1$, R$_2$ and R$_3$ are each independently of one another hydrogen, methyl or ethyl, B is 1,3-phenylene, 1,4-phenylene, 4-sulfo-1,3-phenylene, 3-sulfo-1,4-phenylene, 3,6-disulfo-1,4-phenylene or 4,6-disulfo-1,3-phenylene, X$_1$ is chloro or fluoro, and U is a radical of formula

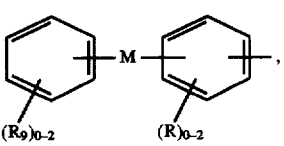
(2a)

wherein (R$_9$)$_{0-2}$ denotes 0 to 2 identical or different radicals R$_9$ selected from the group consisting of methyl, ethyl, methoxy, ethoxy, chloro, sulfo, nitro, hydroxy, carboxy, methoxycarbonyl or ethoxycarbonyl, and $(R)_{0-2}$ denotes 0 to 2 identical or different radicals R selected from the group consisting of sulfo, methyl, methoxy, carboxy and hydroxy, and M is a —CO—NR'—, —NR'—CO—NR'— or —SO$_2$—NR'— group, wherein R' is hydrogen, methyl or ethyl.

A particularly preferred embodiment of this invention relates to compounds of formula (1b') above, wherein $R_1$, $R_2$ and $R_3$ are each hydrogen, $X_1$ is chloro, and U is a radical of formula (2a) above, wherein $(R_9)_{0-2}$ denotes 0 to 2 identical or different radicals $R_9$ selected from the group consisting of methyl, methoxy, sulfo, hydroxy, carboxy and methoxycarbonyl, and $(R)_{0-2}$ denotes 0 to 2 identical or different radicals R selected from the group consisting of sulfo, methyl, methoxy, carboxy and hydroxy, and M is a —CONH— group.

$C_1$–$C_4$Alkyl in formulae (1) to (6b) is generally methyl, ethyl, n- or isopropyl, n-, iso-, sec- or tert-butyl. $C_1$–$C_4$Alkoxy will usually be understood as meaning methoxy, ethoxy, n- or isopropoxy, n-, iso-, sec- or tert-butoxy. Halogen is generally e.g. fluoro, chloro or bromo. $C_1$–$C_4$Alkoxycarbonyl is generally e.g. methoxycarbonyl, ethoxycarbonyl, n- or isopropoxycarbonyl, or n-, iso-, sec- or tert-butoxycarbonyl. Typical examples of $C_1$–$C_4$alkylthio are methylthio or ethylthio. Typical examples of $C_5$–$C_8$cycloalkyl are cyclopentyl or, preferably, cyclohexyl.

The compounds of formula (1) must carry at least one group which is removable with alkali, i.e. they carry e.g. at least one halogen atom at a triazinyl radical or a radical of formula (6a) or (6b) above.

The compounds of formula (1) must further carry at least one sulfo or sulfato group, in which case these compounds can be obtained in the form of the free acid or, preferably, in salt form, typically as sodium, lithium, potassium or ammonium salt.

The compounds of formula (1) are fibre-reactive. By fibre-reactive radicals are meant those radicals that are able to react with the hydroxyl groups of cellulose, with the amino, carboxyl, hydroxyl and thiol groups of wool and silk, or with the amino and, where present, carboxyl groups of synthetic polyamides, to form covalent chemical bonds.

The compounds of formula (1) may be prepared by reacting a compound of formula

          (7), a compound of formula

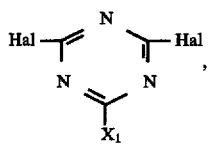          (8a)

a compound of formula

          (9), and, where t=1, additionally a compound of formula

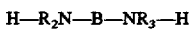          (10) and a compound of formula

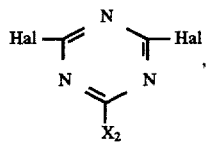          (8b)

wherein U, B, $R_1$, $R_2$, $R_3$, $X_1$ and $X_2$ are each as previously defined, hal is halogen, preferably fluoro or chloro, and T* has the meaning previously given for T, except halogen, with one another, and the sequence of the partial reactions may be freely chosen having regard to the starting compounds.

In the case where t is 1, and T is a radical —NR$_1$—U, and $X_1$ and $X_2$ are identical, about 1 molar equivalent of a compound of formula

          (7)

is first reacted with about 1 molar equivalent of a compound of formula

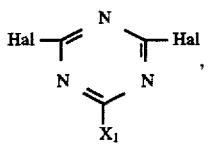          (8a)

and the primary condensate so obtained is then reacted with about 0.5 molar equivalent of a diamine of formula

H—R$_1$N—B—NR$_2$—H          (10), wherein hal, $X_1$, $R_1$, $R_2$, B and U are each as previously defined.

In the case where T is a radical —NR$_1$—U, about 2 molar equivalents of a compound of formula

          (7)

are reacted with about 1 molar equivalent of a compound of formula

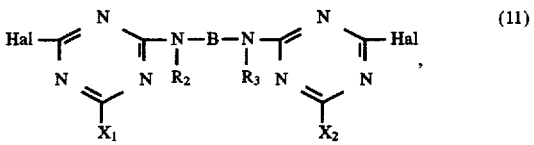          (11)

wherein hal, $X_1$, $X_2$, $R_1$, $R_2$, $R_3$, B and U are each as previously defined.

The conditions to be used in the condensation of the compounds of formulae (7), (9) and (10) with a halotriazine compound are well known in the field of the chemistry of reactive dyes. This reaction is usually carried out in aqueous or aqueous-organic medium in the presence of acid acceptors, conveniently sodium carbonate or sodium hydroxide.

The compounds of formula (8a), (8b), (9), (10) and (11) are known or can be obtained by per se known methods.

The UV absorbers of formula (7) also belong to known classes of compounds and can be prepared in known manner.

The novel UV absorbers of formula (1) are suitable for the photochemical stabilisation of undyed and dyed or printed fibre materials, typically of silk, leather, wool, polyamide or polyurethanes, and, in particular, of cellulosic fibre materials of all kinds. Such fibre materials are typically the natural cellulose fibres such as cotton, linen, jute and hemp, as well as cellulose and regenerated cellulose. Cotton textile fabrics are preferred. The compounds of formula (1) are also suitable for the photochemical stabilisation of hydroxyl group-containing fibres that are components of fibre blends, e.g. blends of cotton and polyester or polyamide fibres. A further preferred field of use relates to the blocking or lessening of UV radiation passing through said textile fabrics (UV cutting) and the increased sun protection that textile fabrics treated with a compound of this invention afford the human skin.

This end is achieved by applying one or more than one compound of formula (1), advantageously in an amount of 0.01 to 5% by weight, preferably of 0.1–3 and, most preferably, of 0.25 to 2% by weight, based on the weight of the fibre material, to the textile material by a conventional dyeing process for reactive dyes. If the textile fabric is a cellulosic material dyed with a reactive dye, then the UV absorber of formula (1) can be applied before, during or after dyeing, preferably simultaneously with the application of the dye.

The novel compounds of formula (1) can be applied to the fibre material and fixed thereon in different manner, preferably in the form of aqueous solutions or print pastes. They are suitable for the exhaust process as well as for pad dyeing. They can be used at low temperature and require only short steaming times in pad-steam processes. Fixation is excellent and non-fixed absorber can be easily washed off, the difference between degree of exhaustion and percentage fixation being remarkably small. The compounds of formula (1) are also suitable for printing, especially on cotton.

The textile materials treated with the compounds of formula (1) have enhanced protection against photochemical fibre degradation and yellowing as well as, in the case of dyed material, enhanced fastness to hot light. The strongly enhanced light stability of the treated textile fabric is to be particularly highlighted. This effect is seen in the fact that, compared with untreated fabric, textile fabric treated with a novel compound of formula (1) has a greatly enhanced sun protection factor (SPR).

The sun protection factor is defined as the quotient of harmful UV radiation without sun protection and harmful UV radiation with sun protection. Accordingly, a sun protection factor is also an indicator of the permeability of the untreated fabric and the fabric treated with a novel compound of formula (1) to UV radiation. The calculation of the sun protection factor of textile fabrics is explained, inter alia, in WO 94/04515 or in J. Soc. Cosmet. Chem. 40, 127–133 (1989) and can be determined in analogous manner.

The invention is illustrated by the following Examples in which temperatures are given in degrees Celsius and parts and percentages are by weight, unless otherwise stated.

EXAMPLE 1

An aqueous solution of 11 g of 5-N-benzoylamino-2-aminobenzenesulfonic acid is run into a suspension of the condensate consisting of 6.45 g of cyanuric chloride and 9.85 g of 4-β-sulfatoethylsulfonylaniline at pH 5.8. The pH of the mixture is kept at 5.8 by the dropwise addition of 15% soda solution and the temperature is raised to about 35°–40° C. When the condensation is complete, the solid contained in the suspension is isolated by filtration, the residue is washed with 5% sodium chloride solution and dried under vacuum, giving a compound of formula

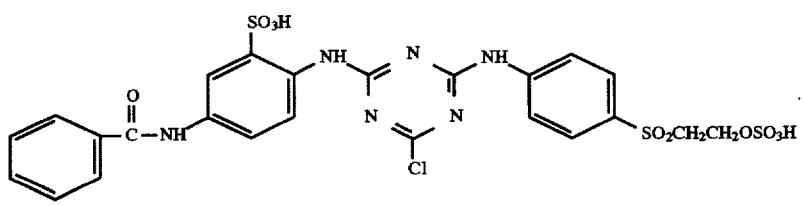

The compound can be applied by a standard method of dyeing with reactive dyes to a cotton tricot. The material so treated has an enhanced sun protection factor as compared to the untreated tricot.

EXAMPLES 2–24

Following the procedure of Example 1, the following compounds can be prepared. Application of these compounds to cotton tricot gives an enhanced sun protection factor compared with untreated fabric.

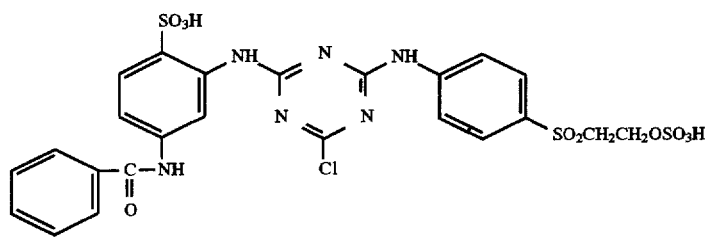
2
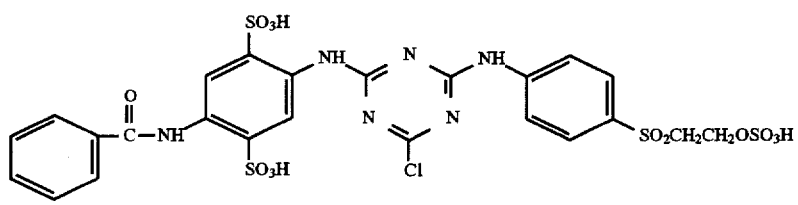
3
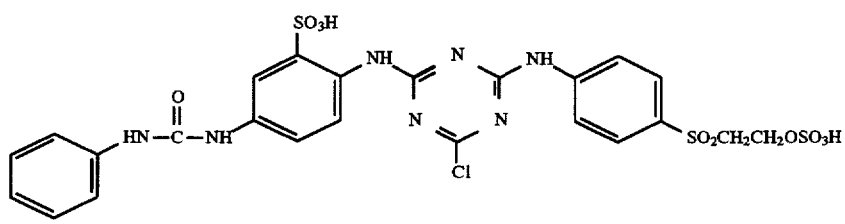
4
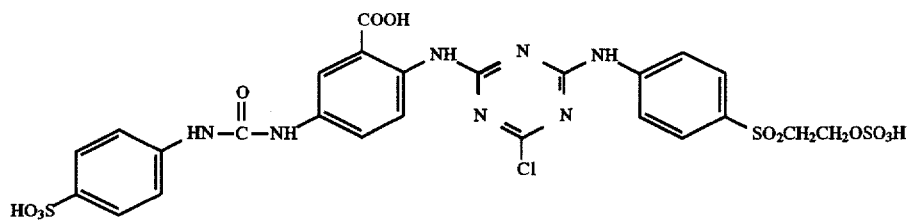
5
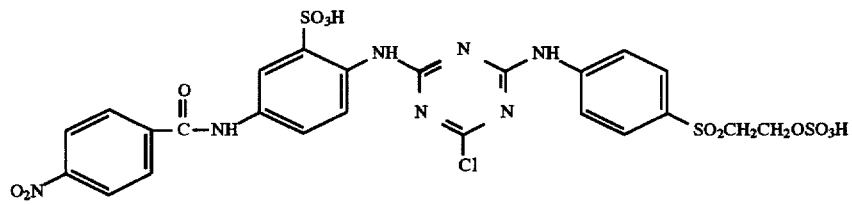
6
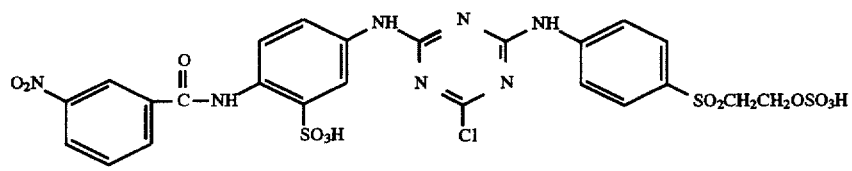
7
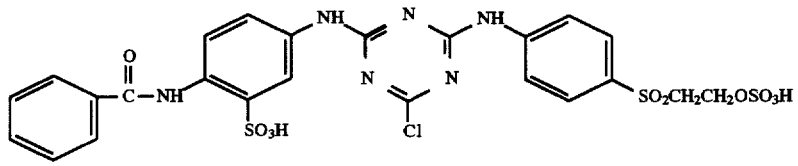
8
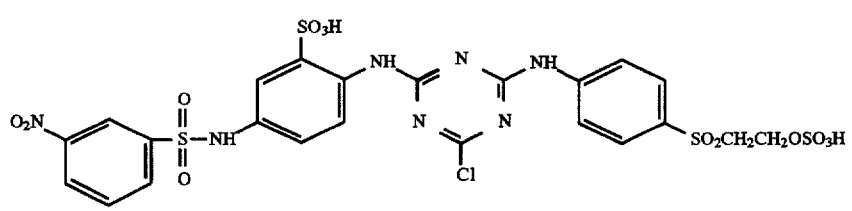
9

-continued
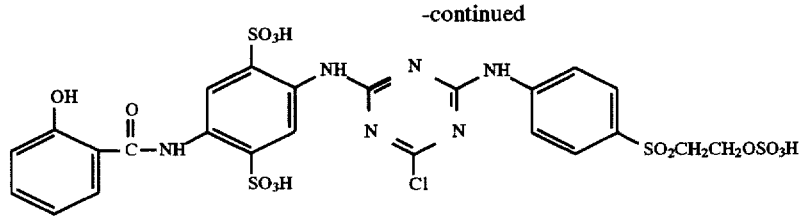
10
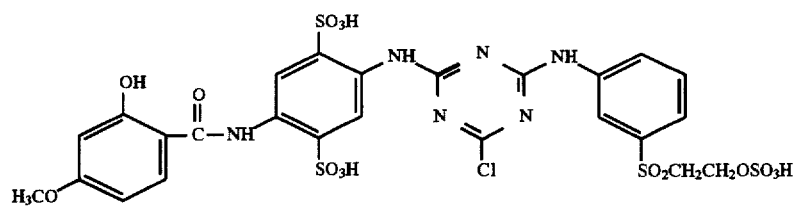
11
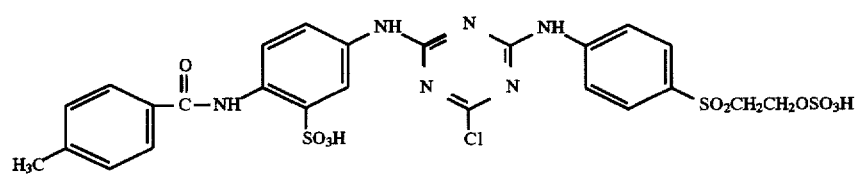
12
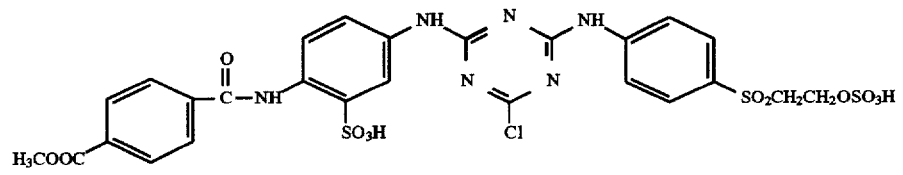
13
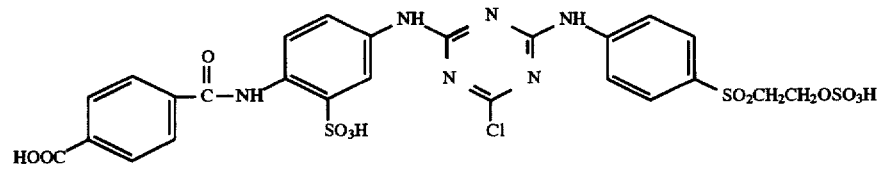
14
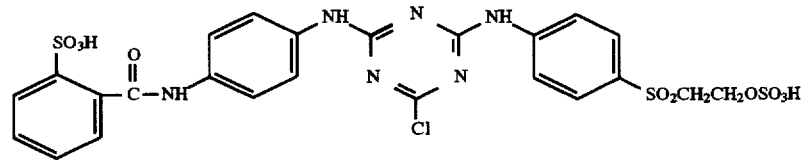
15
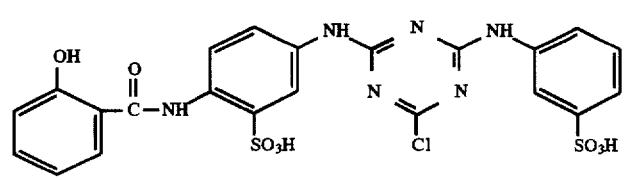
16
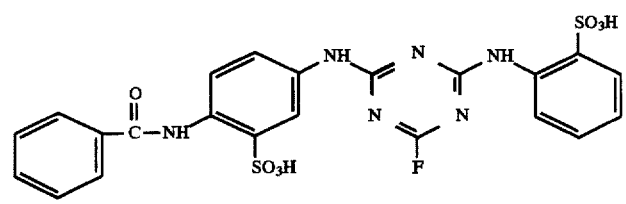
17
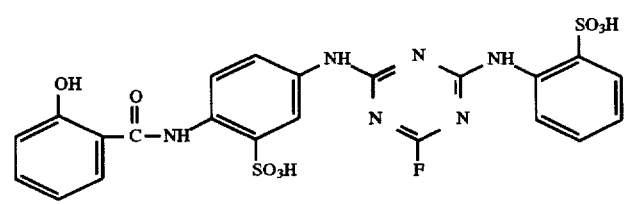
18

-continued
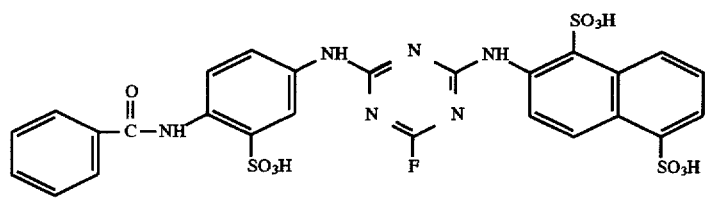 19
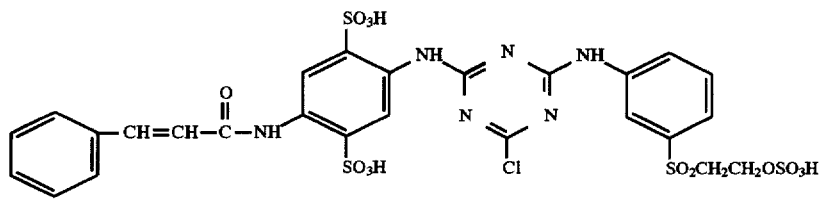 20
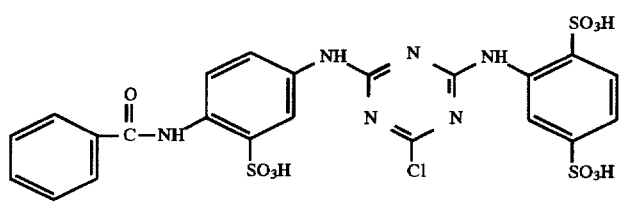 21
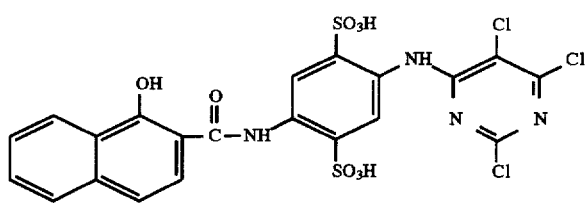 22
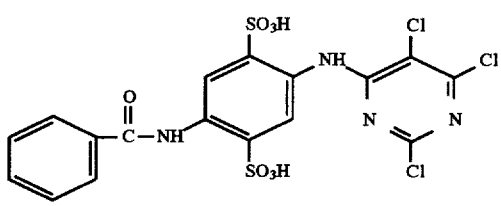 23
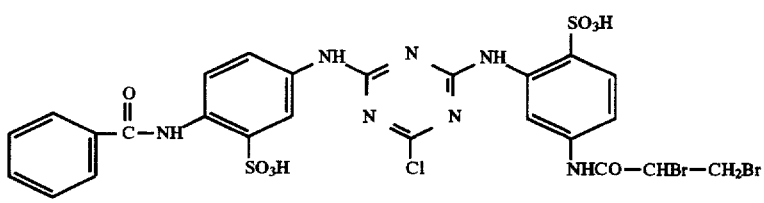 24
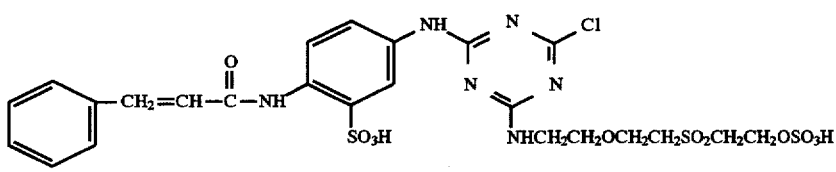 25
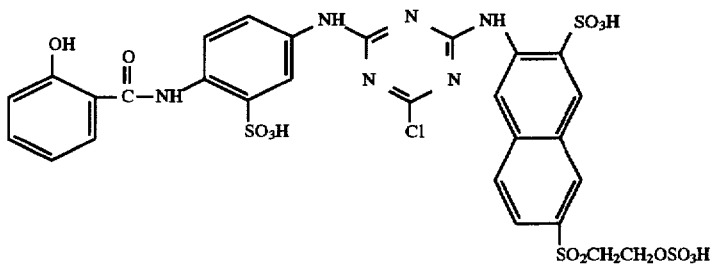 26

-continued

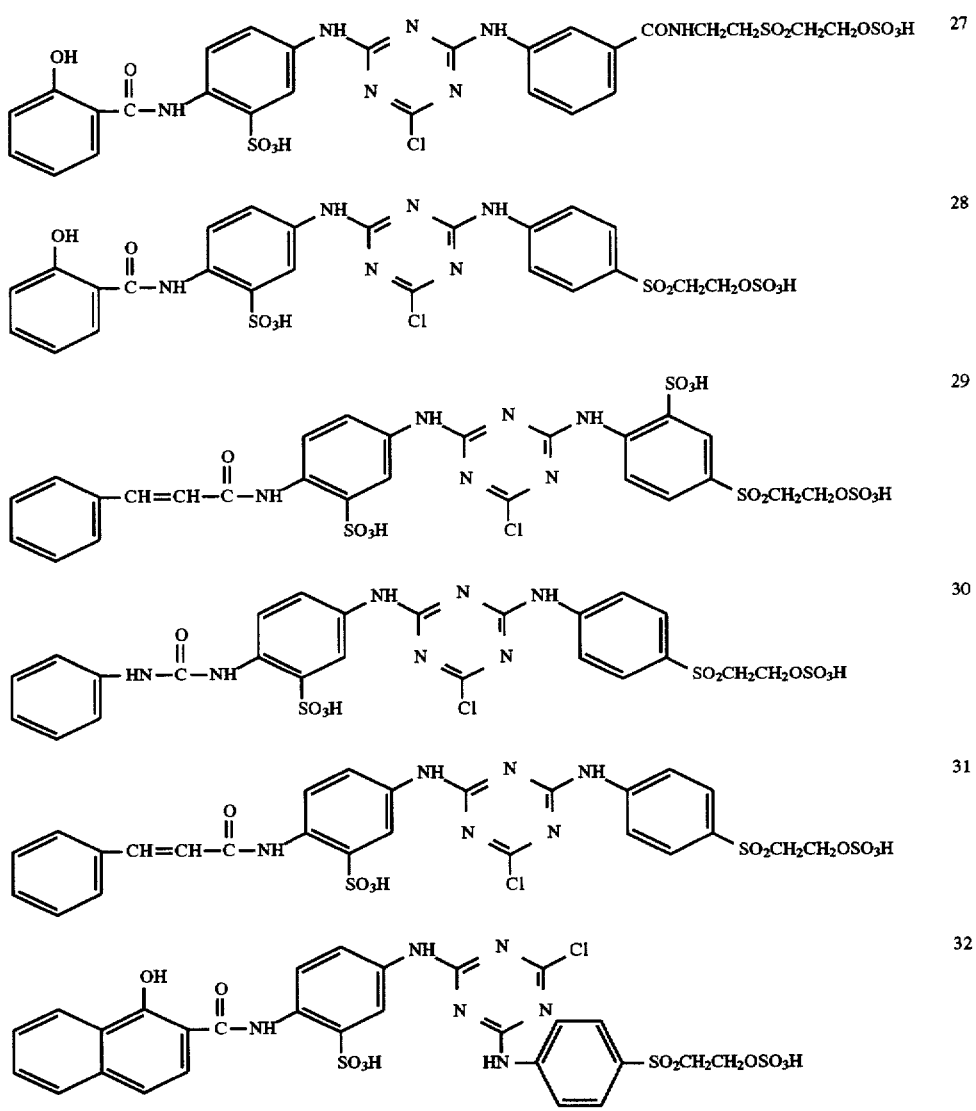

EXAMPLE 33

With rapid stirring, an aqueous solution of 9.43 g of 5 N-benzoylamnino-2-aminobenzenesulfonic acid sodium salt is run into a finely ground suspension of 2.77 g of cyanuric chloride in ice/water over 30 minutes. At the same time, the pH of the mixture is kept at 4 by the dropwise addition of 15% soda solution. After a reaction time of 3 hours the pH of the mixture is increased to 7 and the mixture is heated to 40° C. When the condensation is complete, the solid is isolated by filtration, washed with 5% sodium hydroxide solution and dried under vacuum, giving the compound of formula

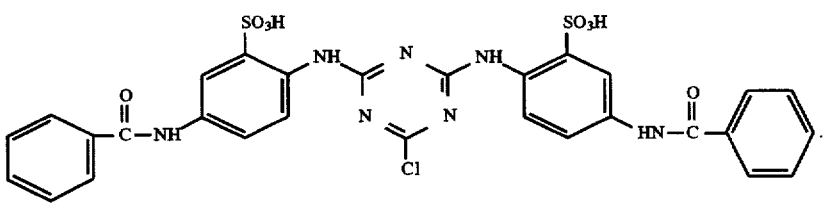

Application of these compounds to cotton tricot gives an enhanced sun protection factor compared with untreated tricot.

EXAMPLE 34

With rapid stirring, an aqueous solution of 11.16 g of 5N-benzoylamino-2-aminobenzene-1,4-disulfonic acid is added dropwise to an ice-cold and finely ground suspension of 5.53 g of cyanuric chloride over 1 hour. At the same time, the pH of the mixture is kept at 4 by the addition of 2N sodium hydroxide solution. When the condensation is complete, the pH is increased to 7 and an aqueous solution of 1.62 g of 1,3-phenylenediamine is added dropwise. The mixture is then heated to 35° C. and stirred for another 1.5 hour. The mixture is cooled to room temperature and salted out with sodium hydroxide. The white precipitate so obtained is isolated by filtration, washed with 5% sodium hydroxide solution and dried under vacuum, giving the compound of formula Application of these compounds to cotton tricot gives an enhanced sun protection factor compared with untreated tricot.

EXAMPLES 35–38

Following the procedure of Example 34, the following compounds can be prepared. Application of these compounds to cotton fabric by a standard method of dyeing with reactive dyes gives an enhanced sun protection factor compared with untreated fabric.

25

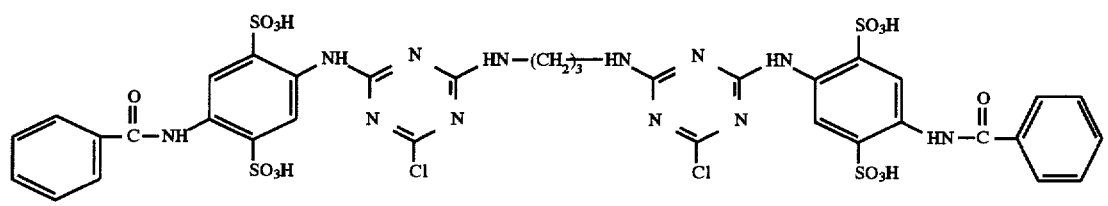

35

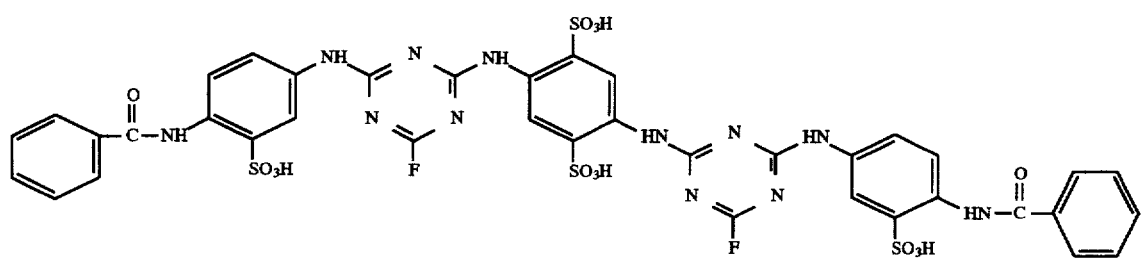

36

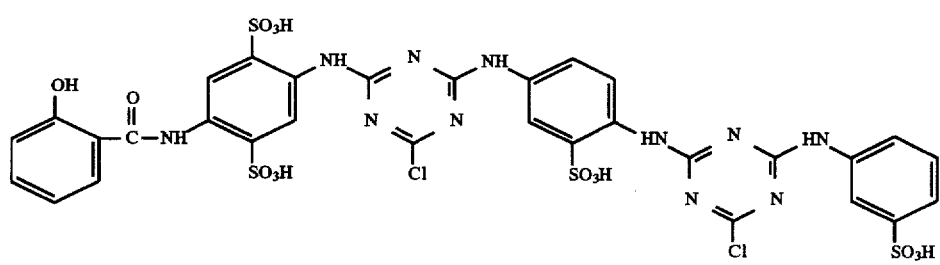

37

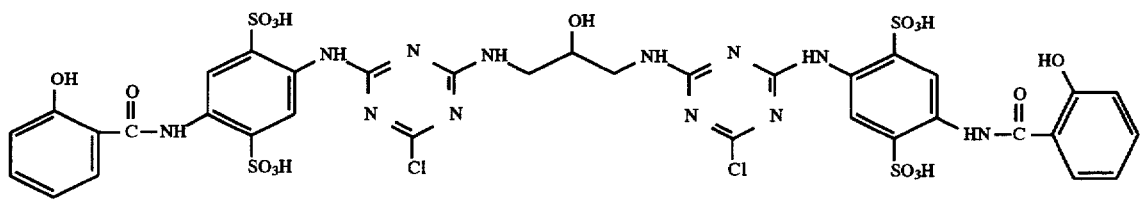

38

APPLICATION EXAMPLE

In a jet dyeing apparatus, 100 g of a bleached cotton tricot are treated for 20 minutes at 60° C. with a liquor containing 1 g of the compound of Example 1 and 75 g of sodium sulfate at a liquor to goods ratio of 1:15. After addition of 30 g of sodium carbonate, the cotton tricot is treated for a further 60 minutes at 60° C. The fabric is then removed from the liquor, washed repeatedly with cold, warm and hot water and dried. The treated tricot has an excellent sun protection factor.

What is claimed is:

1. A compound of formula

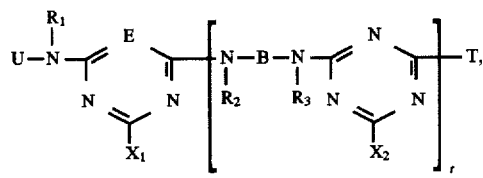

wherein

B is an aliphatic, cycloaliphatic, aromatic or aromatic-aliphatic linking group or, together with —$NR_2$— and —$NR_3$—, forms a piperazine ring, $R_1$, $R_2$ and $R_3$ are each independently of the other hydrogen or $C_1$–$C_4$alkyl which is unsubstituted or substituted by halogen, hydroxy, cyano, $C_1$–$C_4$alkoxy, $C_1$–$C_4$alkoxycarbonyl, carboxy, sulfamoyl, sulfo or sulfato, =E— is a =N— or =C($T_1$)— group, and $T_1$ is halogen, $C_1$–$C_4$alkylsulfonyl, formyl, $C_2$–$C_4$alkoxycarbonyl or cyano, U is the radical of a UV absorber of formula

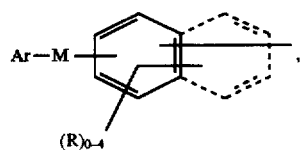

M is a —CO—R'—, —NR'—CO—NR'— or —$SO_2$—NR'— group, R' is hydrogen or $C_1$–$C_4$alkyl, (R)$_{0-4}$ denotes 0 to 4 identical or different radicals R selected from the group consisting of sulfo, $C_1$–$C_4$alkyl, $C_1$–$C_4$alkoxy, carboxy, hydroxy and halogen, Ar is a phenyl, naphthyl or styryl radical which is unsubstituted or substituted by $C_1$–$C_4$alkyl, $C_1$–$C_4$alkoxy, phenoxy which is unsubstituted or substituted by $C_1$–$C_4$alkyl, $C_1$–$C_4$alkoxy, halogen or sulfo, sulfo, carboxy, hydroxy, halogen, nitro, cyano, trifluoromethyl, $C_1$–$C_4$alkoxycarbonyl, formyl, $C_2$–$C_4$alkanoyl, benzoyl, $C_2$–$C_4$alkylcarbonyloxy, sulfamoyl, $C_2$–$C_4$alkanoylamino, benzoylamino, N-mono-$C_1$–$C_4$alkylsulfamoyl, N,N-di-$C_1$–$C_4$alkylsulfamoyl, N-phenylsulfamoyl, $C_1$–$C_4$alkylthio, phenylthio, $C_1$–$C_4$alkylsulfonylamino or phenylsulfonylamino, $X_1$ and $X_2$ are each independently of the other halogen, hydroxy, amino, methylamino, ethylamino, carboxymethylamino, β-sulfoethylamino, N, N-di-β-hydroxyethylamino, cyclohexylamino, o-, m- or p-methylphenylamino, o-, m- or p-methoxyphenylamino, o-, m- or p-sulfophenylamino, 2,4- or 2,5-di-sulfophenylamino, o-carboxyphenylamino, N-ethyl-N-phenylamino, N-methyl-N-phenylamino, 3-carboxypyridin-1-yl or 3-carbamoylpyridin-1-yl, T independently has one of the meanings given for $X_1$ or is a radical U'—$NR_1$'—, wherein U' and R' each independently of the other have the meaning given above for U and $R_1$, or is an alkoxy radical, or a phenoxy radical which is unsubstituted or substituted by $C_1$–$C_4$alkyl, $C_1$–$C_4$alkoxy, halogen, hydroxy, carboxy or sulfo, or an alkylthio radical or phenylthio radical which is unsubstituted or substituted by $C_1$–$C_4$alkyl, $C_1$–$C_4$alkoxy, halogen, hydroxy, carboxy or sulfo radical or a piperidino, piperazino or morpholino radical, or a reactive radical of formula

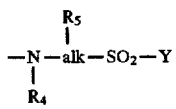 (3a)

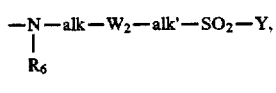 (3b)

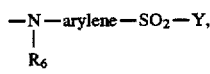 (3c)

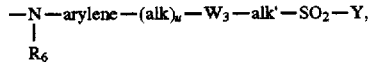 (3d)

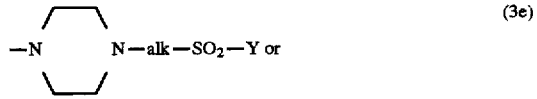 (3e)

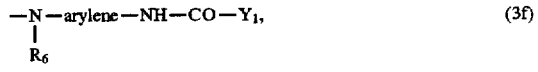 (3f)

$R_4$ is hydrogen, $C_1$–$C_4$alkyl which is unsubstituted or substituted by hydroxy, sulfo, sulfato, carboxy or cyano, or a radical

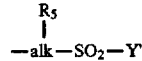

$R_5$ is hydrogen, hydroxy, sulfo, sulfato, carboxy, cyano, halogen, $C_1$–$C_4$alkoxycarbonyl, $C_1$–$C_4$alkanoyloxy, carbamoyl or the —$SO_2$—Y group, $R_6$ is hydrogen or $C_1$–$C_4$alkyl, alk and alk' are each independently of the other $C_1$–$C_6$alkylene, arylene is a phenylene or naphthylene radical which is unsubstituted or substituted by sulfo, carboxy, $C_1$–$C_4$alkyl, $C_1$–$C_4$alkoxy or halogen, Y is vinyl or a radical —$CH_2$—$CH_2$—G, and G is a leaving group, $Y_1$ is the radical —CHBr—$CH_2$—Br or —CBr=$CH_2$, $W_2$ is the radical —O— or —$NR_6$—, $W_3$ is a —$SO_2$—$NR_4$—, —$CONR_4$— or —$NR_4CO$— group, wherein $R_4$ has the meaning given above, and t and u are each independently of the other 0 or 1, with the proviso that the compounds of formula (1) carry at least one sulfo or sulfato group and at least one group which is removable with alkali.

2. A compound according to claim 1, wherein =E— is the =N— group.

3. A compound according to claim 1, wherein B is $C_2$–$C_6$alkylene which is unsubstituted or substituted by hydroxy, sulfo or sulfato, 1,3- or 1,4-phenylene which is unsubstituted or substituted by sulfo, carboxy, chloro, methyl or methoxy, naphthylene which is substituted by 1 or 2 sulfo groups, or a radical of formula

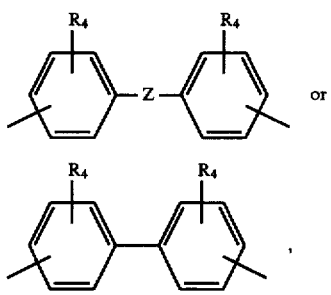
(3a)

or (3b)

wherein Z is —NHCONH—, —O—, —NH—, —CH=CH— or —CH₂—, and R₄ is hydrogen or sulfo.

4. A compound according to claim 3, wherein B is 1,3-phenylene, 1,4-phenylene, 4-sulfo-1,3-phenylene, 3-sulfo-1,4-phenylene, 3,6-disulfo-1,4-phenylene or 4,6-disulfo-1,3-phenylene.

5. A compound according to claim 1, wherein $X_1$ and $X_2$ are each chloro or fluoro.

6. A compound according to claim 1, wherein $R_1$, $R_2$ and $R_3$ are each hydrogen.

7. A compound according to claim 1, wherein U is a radical of formula

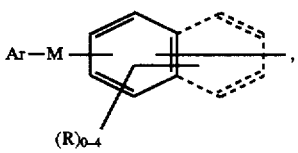
(2)

wherein Ar is a phenyl, naphthyl or styryl radical which is unsubstituted or substituted by $C_1$–$C_4$alkyl; $C_1$–$C_4$alkoxy; phenoxy which is unsubstituted or substituted by $C_1$–$C_4$alkyl, $C_1$–$C_4$alkoxy, halogen or sulfo; sulfo; carboxy; hydroxy; halogen; nitro; cyano; trifluoromethyl; $C_1$–$C_4$alkoxycarbonyl; formyl, $C_2$–$C_4$alkanoyl; benzoyl, $C_2$–$C_4$alkylcarbonyloxy; sulfamoyl; $C_2$–$C_4$alkanoylamino; benzoylamino; n-mono- or N,N-di-$C_1$–$C_4$alkylsulfamoyl; N-phenylsulfamoyl; $C_1$–$C_4$alkylthio; phenylthio; $C_1$–$C_4$alkylsulfonylamino; or phenylsulfonylamino, M is a —CO—NR'—, —NR'—CO—NR'— or —SO₂—NR'— group, R' is hydrogen or $C_1$–$C_4$alkyl, and $(R)_{0-4}$ denotes 0 to 4 identical or different radicals R selected from the group consisting of sulfo, methyl, methoxy, carboxy and hydroxy.

8. A compound according to claim wherein U is a radical of formula

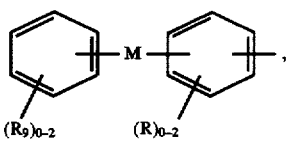
(2a)

wherein $(R_9)_{0-2}$ denotes 0 to 2 identical or different radicals R₉ selected from the group consisting of methyl ethyl, methoxy, ethoxy, chloro, sulfo, nitro, hydroxy, carboxy, methoxycarbonyl or ethoxycarbonyl, and $(R)_{0-2}$ denotes 0 to 2 identical or different radicals R selected from the group consisting of sulfo, methyl, methoxy, carboxy and hydroxy, and M is a —CO—NR'—, —NR'—CO—NR'— or —SO₂—NR'— group, and R' is hydrogen.

9. A compound according to claim 8, wherein U is a radical of formula

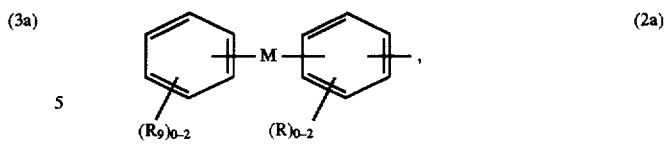
(2a)

wherein $(R_9)_{0-2}$ denotes 0 to 2 identical or different radicals R₉ selected from the group consisting of methyl, methoxy, sulfo, hydroxy, carboxy or methoxycarbonyl, and $(R)_{0-2}$ is 0 to 2 identical or different radicals R selected from the group consisting of sulfo, methyl, methoxy, carboxy and hydroxy, and M is a —CONH— group.

10. A compound according to claim 1, wherein T is amino, methylamino, ethylamino, carboxymethylamino, β-hydroxyethylamino, β-sulfoethylamino, N,N-di-βhydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, mo-, di- or tri-sulfonaphthylamino, morpholino or a radical —NR₁—U, wherein $R_1$ and U are each as claimed in claim 1, or a radical of formulae

(3a)

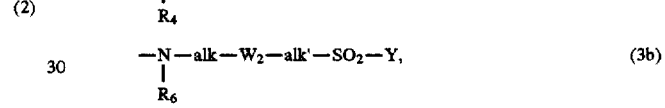
(3b)

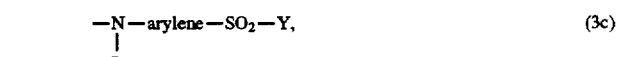
(3c)

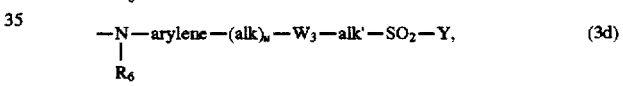
(3d)

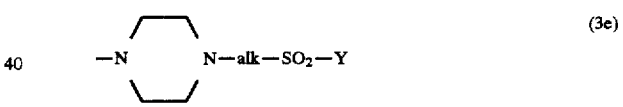
(3e)

or

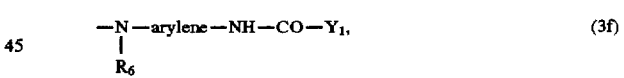
(3f)

wherein $W_3$ is a group of formula —CONH— or —NHCO—, R₄, R₅ and R₆ is each hydrogen, $W_2$ is the radical —O— or —NH—, alk and alk' are each independently of the other ethylene or propylene, arylene is phenylene which is unsubstituted or substituted by methyl, methoxy, carboxy or sulfo, or unsubstituted or sulfo-substituted naphthylene, Y is vinyl or β-sulfatoethyl, and u is 0.

11. A compound according to claim 1, wherein T is a radical —NR₁—U or a radical of formula

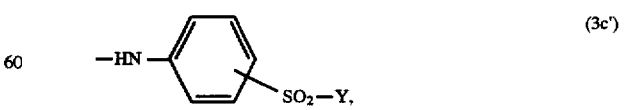
(3c')

wherein $R_1$ is hydrogen or $C_1$–$C_4$alkyl which is unsubstituted or substituted by halogen, hydroxy, cyano, $C_1$–$C_4$alkoxy, $C_1$–$C_4$alkoxycarbonyl, carboxy, sulfamoyl, sulfo or sulfato and U is the radical of a UV absorber of formula

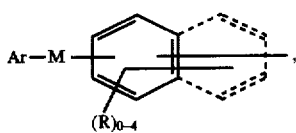

wherein M is a —CO—NR'—, —NR'—CO—NR'— or —SO$_2$—NR'— group, R' is hydrogen or C$_1$–C$_4$alkyl, (R)$_{0-4}$ denotes 0 to 4 identical or different radicals R selected from the group consisting of sulfo, C$_1$–C$_4$alkyl, C$_1$–C$_4$alkoxy, carboxy, hydroxy and halogen, Ar is a phenyl, naphthyl or styryl radical which is unsubstituted or substituted by C$_1$–C$_4$alkyl, C$_1$–C$_4$alkoxy, phenoxy which is unsubstituted or substituted by C$_1$–C$_4$alkalkyl, C$_1$–C$_4$aloxy, halogen or sulfo, sulfo, carboxy, hydroxy, halogen, nitro, cyano, trifluoromethyl, C$_1$–C$_4$alkoxycarbonyl, formyl, C$_2$–C$_4$alkanoyl, benzoyl, C$_2$–C$_4$alkylcarbonyloxy, sulfamoyl, C$_2$–C$_4$alkanoylamino, benzoylamino, N-mono-C$_1$–C$_4$alkylsulfamoyl, N,N-di-C$_1$–C$_4$alkylsulfamoyl, N-phenylsulfamoyl, C$_1$–C$_4$alkylthio, phenylthio, C$_1$–C$_4$alkylsulfonylamino or phenylsulfonylamino, and Y is vinyl or β-sulfatoethyl.

12. A compound according to claim 1 of formula

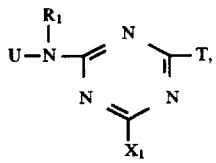

wherein X$_1$ is chloro or fluoro, T is amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, mono-, di- or trisulfonaphthylamino, morpholino or a radical —NR$_1$—U, or a radical of formulae

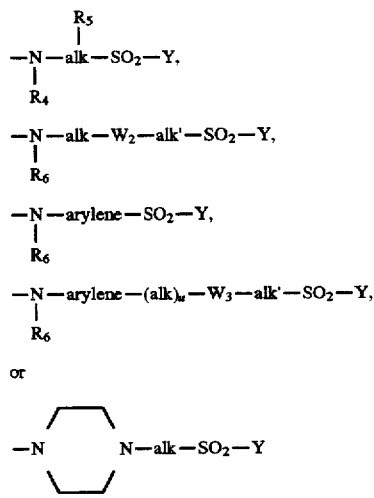

wherein W$_3$ is a group of formula —CONH— or —NHCO—, R$_4$, R$_5$ and R$_6$ are each hydrogen, W$_2$ is the radical —O— or —NH—, alk and alk' are each independently of the other ethylene or propylene, arylene is phenylene which is unsubstituted or substituted by methyl, methoxy, carboxy or sulfo, or unsubstituted or sulfo-substituted naphthylene, Y is vinyl or β-sulfatoethyl, and u is 0, R is hydrogen, and U is a radical of formula

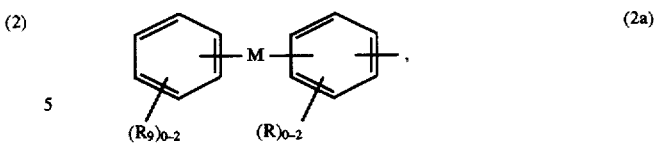

wherein (R$_9$)$_{0-2}$ denotes 0 to 2 identical or different radicals R$_9$ selected from the group consisting of methyl, ethyl, methoxy, ethoxy, chloro, sulfo, nitro, hydroxy, carboxy, methoxycarbonyl or ethoxycarbonyl, and (R)$_{0-2}$ denotes 0 to 2 identical or different radicals R selected from the group consisting of sulfo, methyl, methoxy, carboxy and hydroxy, and M is a —CO—NR'—, —NR'—CO—NR'— or —SO$_2$—NR'— group, wherein R' is hydrogen, methyl or ethyl.

13. A compound according to claim 12 of formula

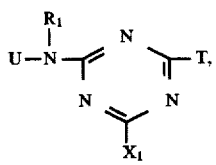

wherein R$_1$ is hydrogen, X$_1$ is chloro, T is a radical —NH—U or a radical of formula

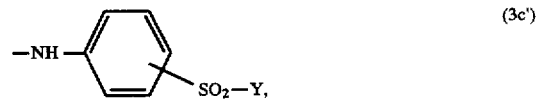

wherein Y is vinyl or β-sulfatoethyl, and U is a radical of formula

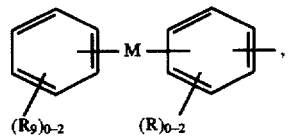

wherein (R$_9$)$_{0-2}$ denotes 0 to 2 identical or different radicals R$_9$ selected from the group consisting of methyl, methoxy, sulfo, hydroxy, carboxy and methoxycarbonyl, and (R)$_{0-2}$ denotes 0 to 2 identical or different radicals R selected from the group consisting of sulfo, methyl, methoxy, carboxy and hydroxy, and M is a —CONH— group.

14. A compound according to claim 1 of formula

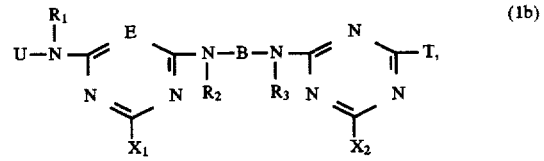

wherein

B is an aliphatic, cycloaliphatic, aromatic or aromatic-aliphatic linking group or, together with —NR$_2$— and —NR$_3$—, forms a piperazine ring, R$_1$, R$_2$ and R$_3$ are each independently of the other hydrogen or C$_1$–C$_4$alkyl which is unsubstituted or substituted by halogen, hydroxy, cyano, C$_1$–C$_4$alkoxy, C$_1$–C$_4$alkoxycarbonyl, carboxy, sulfamoyl, sulfo or sulfato, U is the radical of a UV absorber of formula

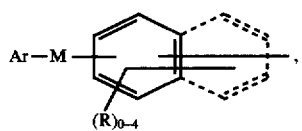

(2)

M is a —CO—NR'—, —NR'—CO—NR'— or —SO$_2$—NR'— group, R' is hydrogen or C$_1$–C$_4$alkyl, (R)$_{0-4}$ denotes 0 to 4 identical or different radicals R selected from the group consisting of sulfo, C$_1$–C$_4$alkyl, C$_1$–C$_4$alkoxy, carboxy, hydroxy and halogen, Ar is a phenyl, naphthyl or styryl radical which is unsubstituted or substituted by C$_1$–C$_4$alkyl, C$_1$–C$_4$alkoxy, phenoxy which is unsubstituted or substituted by C$_1$–C$_4$alkyl, C$_1$–C$_4$alkoxy, halogen or sulfo, sulfo, carboxy, hydroxy, halogen, nitro, cyano, trifluoromethyl, C$_1$–C$_4$alkoxycarbonyl, formyl, C$_2$–C$_4$alkanoyl, benzoyl, C$_2$–C$_4$alkylcarbonyloxy, sulfamoyl, C$_2$–C$_4$alkanoylamino, benzoylamino, N-mono-C$_1$–C$_4$alkylsulfamoyl, N,N-di-C$_1$–C$_4$alklsulfamoyl, N-phenylsulfamoyl, C$_1$–C$_4$alkylthio, phenylthio, C$_1$–C$_4$alkylsulfonylamino or phenylsulfonylamino, X$_1$ and X$_2$ are each independently of the other halogen, hydroxy, amino, methylamino, ethylamino, carboxymethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenvlamino, 2,4- or 2,5-disulfophenylamino, o-carboxvphenylamino, N-ethyl-N-phenylamino, N-methyl-N-phenylamino, 3-carboxypyridin-1-yl or 3-carbamoylpyridin-1-yl, T independently has one of the meanings given for X$_1$ or is a radical U'—NR$_1$'—, wherein U' and R' each independently of the other have the meaning given above for U and R$_1$, or is an alkoxy radical, or a phenoxy radical which is unsubstituted or substituted by C$_1$–C$_4$alkyl, C$_1$–C$_4$alkoxy, halogen, hydroxy, carboxy or sulfo, or an alkylthio radical or phenylthio radical which is unsubstituted or substituted by C$_1$–C$_4$alkyl, C$_1$–C$_4$alkoxy, halogen, hydroxy, carboxy or sulfo radical which or a piperidino, piperazino or morpholino radical, or a reactive radical of formula

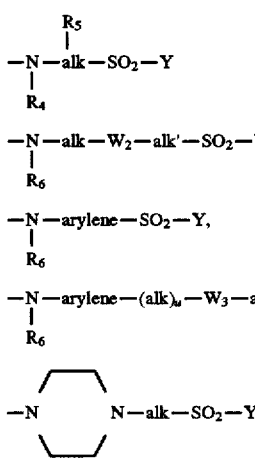

—N—arylene—NH—CO—Y$_1$,   (3f)
|
R$_6$

R$_4$ is hydrogen, C$_1$–C$_4$alkyl which is unsubstituted or substituted by hydroxy, sulfo, sulfato, carboxy or cyano, or a radical R$_5$
    |
—alk—SO$_2$—Y R$_5$ is hydrogen, hydroxy, sulfo, sulfato, carboxy, cyano, halogen, C$_1$–C$_4$alkoxycarbonyl, C$_1$–C$_4$alkanoyloxy, carbamoyl or the —SO2—Y group, R$_6$ is hydrogen or C$_1$–C$_4$alkyl, alk and alk' are each independently of the other C$_1$–C$_6$alkylene, arylene is a phenylene or naphthylene radical which is unsubstituted or substituted by sulfo, carboxy, C$_1$–C$_4$alkyl, C$_1$–C$_4$alkoxy or halogen, Y is vinyl or a radical —CH$_2$—CH$_2$—G, and G is a leaving group, Y$_1$ is the radical —CHBr—CH$_2$—Br or —CBr=CH$_2$, W$_2$ is the radical —O— or —NR$_6$—, W$_3$ is a —SO$_2$—NR$_4$—, —CONR$_4$— or —NR$_4$CO— group, wherein R$_4$ has the meaning given above, and u is 0 or 1.

15. A compound according to claim 1 of formula

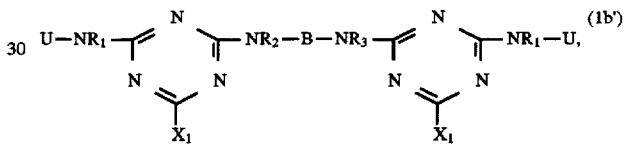

wherein R$_1$, R$_2$ and R$_3$ are each independently of one another hydrogen, methyl or ethyl, B is 1,3-phenylene, 1,4-phenylene, 4-sulfo-1,3-phenylene, 3-sulfo-1,4-phenylene, 3,6-disulfo-1,4-phenylene or 4,6-disulfo-1,3-phenylene, X, is chloro or fluoro, and U is a radical of formula

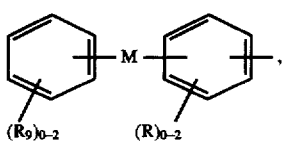

wherein (R$_9$)$_{0-2}$ denotes 0 to 2 identical or different radicals R$_9$ selected from the group consisting of methyl, ethyl, methoxy, ethoxy, chloro, sulfo, nitro, hydroxy, carboxy, methoxycarbonyl or ethoxycarbonyl, and (R)$_{0-2}$ denotes 0 to 2 identical or different radicals R selected from the group consisting of sulfo, methyl, methoxy, carboxy and hydroxy, and M is a —CO—NR'—, —NR'—CO—NR'— or —SO$_2$—NR'— group, wherein R' is hydrogen, methyl or ethyl.

* * * * *